(12) United States Patent
Nieuwoudt et al.

(10) Patent No.: US 6,395,141 B1
(45) Date of Patent: May 28, 2002

(54) SEPARATION OF COMPONENTS FROM AROMATIC HYDROCARBON MIXTURES THEREOF BY EXTRACTIVE DISTILLATION

(76) Inventors: Izak Nieuwoudt; Braam van Dyk, both of 2 Tertius Street, Amandaglen Durbanville 7550 (ZA)

( * ) Notice: Subject to any disclaimer, the term of this patent is extended or adjusted under 35 U.S.C. 154(b) by 0 days.

(21) Appl. No.: 09/671,333

(22) Filed: Sep. 28, 2000

Related U.S. Application Data

(63) Continuation of application No. PCT/IB00/00075, filed on Jan. 26, 2000, and a continuation-in-part of application No. PCT/IB00/00078, filed on Jan. 26, 2000.

(30) Foreign Application Priority Data

| Jan. 28, 1999 | (ZA) | ................................................. 99/0654 |
|---|---|---|
| Jan. 28, 1999 | (ZA) | ................................................. 99/0655 |
| Jan. 28, 1999 | (ZA) | ................................................. 99/0656 |
| Jan. 28, 1999 | (ZA) | ................................................. 99/0657 |
| Jan. 28, 1999 | (ZA) | ................................................. 99/0658 |
| Jan. 28, 1999 | (ZA) | ................................................. 99/0659 |

(51) Int. Cl.[7] .............................. B01D 3/40; C07C 7/08
(52) U.S. Cl. ........................ 203/57; 203/60; 203/62; 203/58; 585/804; 585/864; 585/865; 585/866
(58) Field of Search .................... 203/60, 61, 58, 203/57, 62, 100; 585/865, 866, 864, 800, 804

(56) References Cited

U.S. PATENT DOCUMENTS

| 2,636,050 A | | 4/1953 | Hoaglin et al. |
| 3,816,302 A | * | 6/1974 | Paret .......................... 208/323 |
| 4,053,369 A | * | 10/1977 | Cines .......................... 203/64 |
| 4,081,355 A | * | 3/1978 | Preusser et al. ............... 203/58 |
| 4,363,704 A | * | 12/1982 | Berg ........................... 203/60 |
| 4,379,028 A | | 4/1983 | Berg et al. |
| 4,431,838 A | | 2/1984 | Feldman et al. |
| 4,514,262 A | | 4/1985 | Berg |
| 4,559,109 A | | 12/1985 | Lee et al. |
| 4,584,063 A | | 4/1986 | Berg et al. |
| 4,620,901 A | | 11/1986 | Berg et al. |
| 4,676,875 A | * | 6/1987 | Berg et al. .................. 585/805 |
| 5,145,562 A | | 9/1992 | Brown et al. |
| 5,453,166 A | | 9/1995 | Berg |
| 5,800,681 A | | 9/1998 | Berg |
| 5,897,750 A | | 4/1999 | Berg |

FOREIGN PATENT DOCUMENTS

| EP | 0 047 204 A2 | 3/1982 |
| EP | 0 496 060 A2 | 9/1992 |
| GB | 877 360 | 9/1961 |
| JP | 54 119 411 | 9/1979 |

OTHER PUBLICATIONS

Cepeda E Et Al: "Separacion por destilacion extractiva de mezclas formadas por alcoholes y sus esteres del acido acetico", An. Quim., Ser. A (AQSTDQ, 02111330): 1984; vol. 80 (3, Suppl. 2); Pp. 755–759, XP000908880; Col. Univ. Alava; Dep. Quim. Tecn.; Vitoria; Spain (ES) (See English summary on p. 755).

* cited by examiner

*Primary Examiner*—Virginia Manoharan
(74) *Attorney, Agent, or Firm*—Larson & Taylor PLC

(57) ABSTRACT

A method of separating aromatic hydrocarbons and non-aromatic hydrocarbons, and aromatic hydrocarbons and naphtenes involves distilling a mixture of the components by an extractive distillation process in the presence of an extractive distillation solvent. The extractive distillation solvent may be an ester of a dibasic acid, an acetonyl acetone or morpholine.

10 Claims, 1 Drawing Sheet

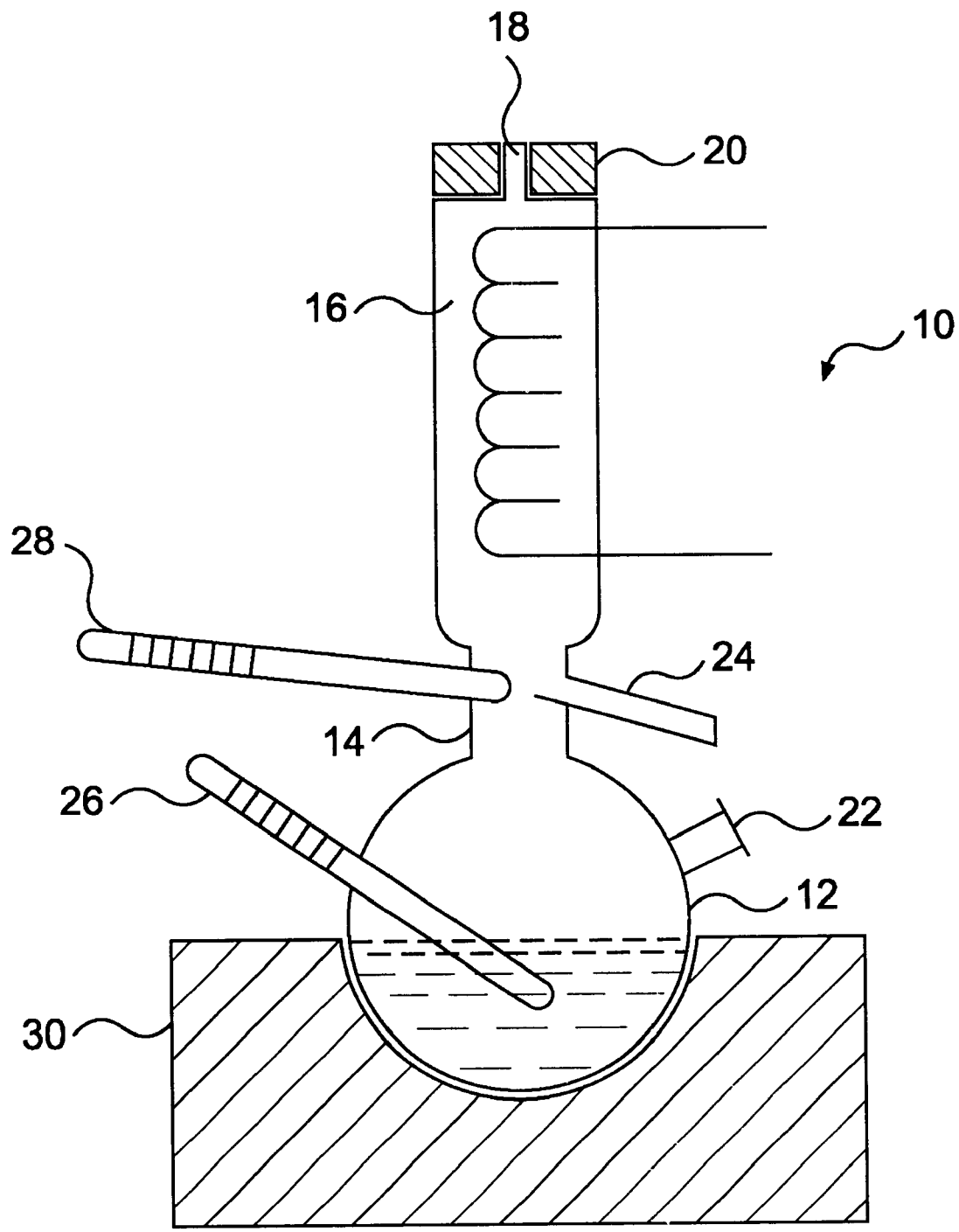

SEPARATION OF COMPONENTS FROM AROMATIC HYDROCARBON MIXTURES THEREOF BY EXTRACTIVE DISTILLATION

This is a continuation of International PCT Application Numbers PCT/IB00/00075 and PCT/IB00/00078, filed on Jan. 26, 2000.

FIELD OF INVENTION

The present invention relates to the separation of components from aromatic hydrocarbon mixtures thereof by extractive distillation.

BACKGROUND TO INVENTION

Extractive distillation is a process to separate close-boiling compounds from each other by introducing a selectively-acting third component, the extractive distillation solvent, with the result that the relative volatility of the mixture to be separated is increased and azeotropes, if present, are overcome. The extractive distillation solvent is to be selected such that it does not form an undesired azeotrope with any of the compounds in the mixture.

As an example, the separation of C7, C8-isomers (non-aromatic hydrocarbons) and toluene (aromatic hydrocarbons) is complicated due to low relative volatilitles or the existence of an azeotrope. Aniline or phenol have been proposed in the literature as extractive distillation solvents to produce C7, C8-isomers as distillate.

As an example, the separation of benzene (aromatic hydrocarbons) and cyclohexane (naphtenes) is complicated due to the existence of an azeotrope. Aniline has been proposed in the literature as extractive distillation solvents to produce cyclohexane as distillate.

As has been stated in U.S. Pat. No. 5,800,681 (Berg) extractive distillation is the method of separating close boiling compounds from each other by carrying out the distillation in a multiplate rectification column in the presence of an added liquid or liquid mixture, said liquid(s) having a boiling point higher than the compounds being separated. The extractive distillation solvent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive distillation solvent should boil higher than any of the close boiling liquids being separated and not form minimum azeotropes with them. Usually the extractive distillation solvent is introduced a few plates from the top of the column to ensure that none of the extractive distillation solvent is carried over with the lowest boiling component.

It is an object of this invention to suggest at least one further extractive distillation solvent for the separation of components from mixtures thereof.

SUMMARY OF INVENTION

According to the invention, a method of separation of aromatic hydrocarbons and non-aromatic hydrocarbons, includes the step of distilling a mixture of aromatic hydrocarbons and non-aromatic hydrocarbons containing at least aromatic hydrocarbons and non-aromatic hydrocarbons by way of an extractive distillation process in the presence of an extractive distillation solvent being an ester of a dibasic acid.

The aromatic hydrocarbons and non-aromatic hydrocarbons mixture may contain only aromatic hydrocarbons and non-aromatic hydrocarbons.

The non-aromatic hydrocarbons may be at least one of the compounds selected from a group consisting of C7-isomers and C8-isomers.

The aromatic hydrocarbons may be toluene.

The ester of a dibasic acid may be selected from a group consisting of dimethylmaleate and dimethylphtalate.

Also according to the invention, a method of separation of aromatic hydrocarbons and non-aromatic hydrocarbons includes the step of distilling a mixture of aromatic hydrocarbons excluding benzene and non-aromatic hydrocarbons containing at least aromatic hydrocarbons excluding benzene and non-aromatic hydrocarbons by way of an extractive distillation process in the presence of an extractive distillation solvent being N-methyl 2-pyrrolidone.

The aromatic hydrocarbons/non-aromatic hydrocarbons mixture may contain only aromatic hydrocarbons and non-aromatic hydrocarbons.

The non-aromatic hydrocarbons may be least one of the compounds selected from a group consisting of C7-isomers and C8-isomers.

The aromatic hydrocarbons may be toluene.

The non-aromatic hydrocarbons may be naphtenes and the extractive distillation solvent may be selected from the group consisting of a dione, an ester of a dibasic acid and a morpholine.

The aromatic hydrocarbons and naphtenes mixture may contain only aromatic hydrocarbons and naphtenes.

The aromatic hydrocarbons may be benzene.

The naphtenes may be cyclohexane.

The dione may be acetonyl acetone.

The ester of a dibasic acid may be selected from a group consisting of dimethylmaleate and dimethylphtalate.

BRIEF DESCRIPTION OF DRAWING

The invention will now be described by way of example with reference to the accompanying schematic drawing.

In the drawing there is shown a schematic view of an experimental apparatus for testing an extractive distillation solvent for separating components from mixtures thereof in accordance with the invention.

DETAILED DESCRIPTION OF THE PREFERRED EMBODIMENTS

In the drawing there is shown a vapour-liquid equilibrium still 10 including a bulb flask 12 having a tube 14 leading to a condenser 16 and terminating in an outlet 18. The outlet 18 has an electromagnetic closure mechanism 20.

A liquid phase sample conduit 22 leads into the flask 12.

A further liquid phase sample conduit 24 leads into the tube 14.

A first thermometer 26 is adapted to read the temperature of the liquid contained in the flask 12, and a second thermometer 28 is adapted to read the temperature of the vapour in the tube 14.

The flask 12 can be heated by a heating mantle 30.

The extractive distillation procedure is as follows:

A liquid mixture is prepared consisting of the components to be separated and an extractive distillation solvent. The liquid is introduced into the bulb flask 12 via conduit 22.

The mixture in the bulb flask 12 is then heated by the heating mantle 30 and kept at boiling point.

During boiling the mixture separates into a liquid phase remaining in the bulb flask 12 and a vapour phase in the tube 14. In the tube 14 the vapour phase is cooled by the condenser 16, whereafter it condenses and returns as liquid to the bulb flask 12.

The mixture is boiled and condensed for several hours, normally 5 to 6 hours. The process of evaporation and condensation is repeated until equilibrium is reached between the vapour and liquid phases. Thereafter, a liquid sample of the liquid phase in the bulb flask 12 is extracted through conduit 22 and a liquid sample of the condensed vapour phase in the tube 14 is extracted through conduit 24.

The temperature of the liquid phase in the bulb flask 12 is continuously monitored by the thermometer 26, and the temperature of the vapour phase in the tube 14 is continuously monitored by the thermometer 28.

EXPERIMENT 1

A C7, C8-isomers/toluene liquid mixture with a molar ratio of 0.96:1 has a relative volatility of 1.41.

The separation was effected by using a suitable ester of a dibasic acid as an extractive distillation solvent.

A mixture of C7, C8-isomers (19.1 g), toluene (18.4 g) and Dimethylphtalate (266.2 g) was charged into the flask 12 of the vapour-liquid equilibrium still 10 and the above procedure was applied. The liquid and vapour phases were analysed. The liquid and vapour molar fractions were determined to be as follows:

TABLE 1

| Component | Liquid (mole fraction) | Vapour (mole fraction) |
|---|---|---|
| C7, C8-isomers | 0.108 | 0.868 |
| Toluene | 0.113 | 0.132 |
| Dimethylphtalate | 0.778 | 0.00 |

This translates to a relative volatility of 6.89 for the system C7, C8-isomers/toluene in the ternary system shown above, the C7, C8-isomers being the distillate.

EXPERIMENT 2

A C7, C8-isomers/toluene mixture with a molar ratio of 1.1:1 has a relative volatility of 1.38.

The separation was effected by using N-methyl-2-pyrolidone (NMP) as an extractive distillation solvent.

A mixture of C7, CS-isomers (30.2 g), toluene (25.2 g) and NMP (208.8 g) was charged into the flask 12 of the vapour-liquid equilibrium still 10 and the above procedure was applied. The liquid and vapour phases were analysed. The liquid and vapour molar fractions were determined to be as follows:

TABLE 2

| Component | Liquid (mole fraction) | Vapour (mole fraction) |
|---|---|---|
| C7, C8-isomers | 0.183 | 0.874 |
| Toluene | 0.166 | 0.124 |
| NMP | 0.651 | 0.002 |

This translates to a relative volatility of 6.36 for the system C7, C8-isomer/toluene in the ternary system shown above, the C7, C8-isomers being the distillate.

EXPERIMENT 3

An 2,2,4-trimethylpentane/toluene mixture with a molar ratio of 1:1.06 has a relative volatility of 1.38.

The separation was effected by using N-methyl-2-pyrrolidone as an extractive distillation solvent.

A mixture of 2,2,4-trimethylpentane (19.3 g), toluene (16.5 g) and NMP (130.4 g) was charged into the flask 12 of the vapour-liquid equilibrium still 10 and the above procedure was applied. The liquid and vapour phases were analysed. The liquid and vapour molar fractions were determined to be as follows:

TABLE 3

| Component | Liquid (mole fraction) | Vapour (mole fraction) |
|---|---|---|
| 2,2,4-trimethylpentane | 0.102 | 0.752 |
| Toluene | 0.108 | 0.198 |
| NMP | 0.791 | 0.050 |

This translates to a relative volatility of 4.04 for the system 2,2,4-trimethylpentane/toluene in the ternary system shown above, the 2,2,4-trimethylpentane being the distillate.

EXPERIMENT 4

An 2,2,4-trimethylpentane/toluene mixture with a molar ratio of 1:1.16 has a relative volatility of 1.40.

The separation was effected by using a suitable ester of a dibasic acid such as dimethylmaleate as an extractive distillation solvent.

A mixture of 2,2,4-trimethylpentane (22.9 g), toluene (21.4 g) and dimethylmaleate (226.5 g) was charged into the flask 12 of the vapour-liquid equilibrium still 10 and the above procedure was applied. The liquid and vapour phases were analysed. The liquid and vapour molar fractions were determined to be as follows:

TABLE 4

| Component | Liquid (mole fraction) | Vapour (mole fraction) |
|---|---|---|
| 2,2,4-trimethylpentane | 0.100 | 0.750 |
| Toluene | 0.116 | 0.222 |
| Dimethylmaleate | 0.784 | 0.027 |

This translates to a relative volatility of 3.91 for the system 2,2,4-trimethylpentane/toluene in the ternary system shown above, the 2,2,4-trimethylpentane being the distillate.

EXPERIMENT 5

An 2,2,4-trimethylpentaneltoluene mixture with a molar ratio of 1:1.16 has a relative volatility of 1.40.

The separation was effected by using a suitable ester of a dibasic acid such as dimethylphtalate as an extractive distillation solvent.

A mixture of 2,2,4-trimethylpentane (18.9 g), toluene (14.9 g) and dimethylphtalate (246.8 g) was charged into the flask 12 of the vapour-liquid equilibrium still 10 and the above procedure was applied. The liquid and vapour phases were analysed. The liquid and vapour molar fractions were determined to be as follows:

TABLE 5

| Component | Liquid (mole fraction) | Vapour (mole fraction) |
|---|---|---|
| 2,2,4-trimethylpentane | 0.104 | 0.763 |
| Toluene | 0.101 | 0.237 |
| Dimethylphtalate | 0.795 | 0.000 |

This translates to a relative volatility of 3.15 for the system 2,2,4-trimethylpentane/toluene in the ternary system shown above, the 2.2,4-trimethylpentane being the distillate.

EXPERIMENT 6

A cyclohexane/benzene liquid mixture with a molar ratio of 1:1 has a relative volatility of 0.97.

The separation was effected by using a suitable dione as, an extractive distillation solvent.

A mixture of cyclohexane (34.8 g), benzene (33.2 g) and acetonylacetone (181.1 g) was charged into the flask 12 of the vapour-liquid equilibrium still 10 and the above procedure was applied. The liquid and vapour phases were analysed. The liquid and vapour molar fractionss were determined to be as follows:

TABLE 6

| Component | Liquid (mole fraction) | Vapour (mole fraction) |
|---|---|---|
| Benzene | 0.175 | 0.173 |
| Cyclohexane | 0.171 | 0.821 |
| Acetonylacetone | 0.654 | 0.006 |

This translates to a relative volatility of 4.87 for the system cyclohexane/benzene in the ternary system shown above, the cyclohexane being the distillate.

EXPERIMENT 7

A benzene/cyclohexane mixture with a molar ratio of 1:1 has a relative volatility of 0.97.

The separation was effected by using a suitable ester of a dibasic acid as an extractive distillation solvent.

A mixture of cyclohexane (24.9 g), benzene (24.6 g) and dimethylmaleate (339.0 g) was charged into the flask 12 of the vapour-liquid equilibrium still 10 and the above procedure was applied. The liquid and vapour phases were analysed. The liquid and vapour molar fractions were determined to be as follows:

TABLE 7

| Component | Liquid (mole fraction) | Vapour (mole fraction) |
|---|---|---|
| Cyclohexane | 0.100 | 0.654 |
| Benzene | 0.106 | 0.335 |
| Dimethylmaleate | 0.794 | 0.011 |

This translates to a relative volatility of 2.06 for the system benzenelcyclohexane in the ternary system shown above, the cyclohexane being the distillate.

EXPERIMENT 8

A cyclohexanelbenzene mixture with a molar ratio of 0.63:1 has a relative volatility of 1.05.

The separation was effected by using morpholine as an extractive distllation solvent.

A mixture of cyclohexane (22.5 g), benzene (22.0 g) and morpholine (175.5 g) was charged into the flask 12 of the vapour-liquid equilibrium still 10 and the above procedure was applied. The liquid and vapour phases were analysed. The liquid and vapour molar fractions were determined to be as follows:

TABLE 8

| Component | Liquid (mole fraction) | Vapour (mole fraction) |
|---|---|---|
| Cyclohexane | 0.049 | 0.585 |
| Benzene | 0.077 | 0.415 |
| Morpholine | 0.874 | 0.000 |

This translates to a relative volatility of 2.21 for the system cyclohexanelbenzene in the ternary system shown above, the cyclohexane being the distillate.

EXPERIMENT 9

A benzenelcyclohexane mixture with a molar ratio of 1:1.37 has a relative volatility of 0.92.

The separation was effected by using a suitable ester of a dibasic acid as an extractive distillation solvent.

A mixture of benzene (13.5 g), cyclohexane (20.0 g) and dimethylphthalate (268.4 g) was charged into the flask 12 of the vapour-liquid equilibrium still 10 and the above procedure was applied. The liquid and vapour phases were analysed. The liquid and vapour molar fractions were determined to be as follows:

TABLE 9

| Component | Liquid (mole fraction) | Vapour (mole fraction) |
|---|---|---|
| Benzene | 0.099 | 0.326 |
| Cyclohexane | 0.136 | 0.674 |
| Dimethylphthalate | 0.764 | 0.000 |

This translates to a relative volatility of 1.50 for the system cyclohexane/benzene in the ternary system shown above, the cyclohexane being the distillate.

What is claimed is:

1. A method of separation of aromatic hydrocarbons and non-aromatic hydrocarbons, consisting of distilling a mixture of aromatic hydrocarbons and non-aromatic hydrocarbons containing at least aromatic hydrocarbons and non-aromatic hydrocarbons by an extractive distillation process in the presence of an extractive distillation solvent selected from the group consisting of dimethylmaleate and dimethylphtalate.

2. The method as claimed in claim 1, wherein the aromatic hydrocarbons and non-aromatic hydrocarbons mixture contains only aromatic hydrocarbons and non-aromatic hydrocarbons.

3. The method as claimed in claim 1, wherein the non-aromatic hydrocarbons comprise at least one of the compounds selected from the group consisting of C7-isomers and C8-isomers.

4. The method as claimed in claim 1, wherein the aromatic hydrocarbons comprise toluene.

5. A method as claimed in claim 1, wherein the aromatic hydrocarbons comprise benzene.

6. A method as claimed in claim 1, wherein the non-aromatic hydrocarbons comprise cyclohexane.

7. A method of separation of aromatic hydrocarbons and naphtenes, comprising distilling a mixture of aromatic hydrocarbons and naphtenes containing at least aromatic hydrocarbons and naphtenes by an extractive distillation process in the presence of an extractive distillation solvent selected from the group consisting of acetonyl acetone and morpholine.

8. The method as claimed in claim 7, wherein the aromatic hydrocarbons and naphtenes mixture contains only aromatic hydrocarbons and naphtenes.

9. The method as claimed in claim 7, wherein the aromatic hydrocarbons comprise benzene.

10. The method as claimed in claim 7, wherein the naphtenes comprise cyclohexane.

\* \* \* \* \*